(12) United States Patent
Fesus et al.

(10) Patent No.: US 6,506,796 B1
(45) Date of Patent: Jan. 14, 2003

(54) USE OF A RAR-γ-SPECIFIC AGONIST LIGAND FOR INCREASING THE RATE OF APOPTOSIS

(75) Inventors: Laszlo Fesus, Debrecen (HU); Zsuzsa Szondy, Debrecen (HU); Uwe Reichert, Pont-du-Loup (FR)

(73) Assignee: Centre International de Recherches Dermatologiques Galderma, Valbonne (FR)

(*) Notice: Subject to any disclaimer, the term of this patent is extended or adjusted under 35 U.S.C. 154(b) by 49 days.

(21) Appl. No.: 09/624,771

(22) Filed: Jul. 25, 2000

Related U.S. Application Data

(62) Division of application No. 09/051,407, filed as application No. PCT/FR96/01568 on Oct. 8, 1996.

(30) Foreign Application Priority Data

Oct. 9, 1995 (FR) .......................................... 95 12179

(51) Int. Cl.$^7$ ................................................ A01N 25/00
(52) U.S. Cl. ....................... 514/510; 514/825; 514/826; 514/863; 514/866; 514/903
(58) Field of Search ................................ 514/423, 825, 514/826, 863, 866, 903

(56) References Cited

FOREIGN PATENT DOCUMENTS

WO          97 03682          2/1997

OTHER PUBLICATIONS

Oncogene, vol. 11, No. 3, 1995, pp. 493–504, XP000575582, Z–M. Shad et al, "P53 independent GO/G1 arrest and apoptosis induced by a novel retinoid in human breast cancer cells."

J. Clin. Invest., vol. 93, No. 5, 1994, pp. 1981–1986, XP000646558, J. Corbeil et al, "antiproliferative effect of retinoid compounds on Kaposi's sarcoma cells".

J. Med. Chem., vol. 38, No. 16, 1995, pp. 3146–3155, XP000615461, M.F. Boehm et al, "Design and synthesis of potent retinoid–X receptor selective ligands that induce apoptosis in leukemia cells".

*Primary Examiner*—Johann Richter
*Assistant Examiner*—Everett White
(74) *Attorney, Agent, or Firm*—Burns, Doane, Swecker & Mathis, L.L.P.

(57) ABSTRACT

Methods of cosmetically or therapeutically treating diseases or disorders in cell populations whose pathology is linked to an inadequate rate of apoptosis by administering a therapeutically effective amount of 6-3-(1-adamantyl)-4-hydroxyphenyl)-2-naphthanoic acid.

18 Claims, No Drawings

USE OF A RAR-γ-SPECIFIC AGONIST LIGAND FOR INCREASING THE RATE OF APOPTOSIS

This application is a divisional, of application Ser. No. 09/051,407, filed Jul. 15, 1998 which is a 371 of PCT/FR96/01568 filed Oct. 8, 1996.

The present invention relates to the use of specific retinoids in the preparation of a pharmaceutical composition which is intended to increase the rate of apoptosis. These retinoids can also be used in cosmetic compositions which are intended, in particular, to prevent and/or combat photo-induced or chronological ageing of the skin.

Two types of mechanism are involved in the death of cells. The first, which is the classical type, is termed necrosis. Morphologically, necrosis is characterized by swelling of the mitochondria and the cytoplasm and by nuclear distortion, followed by destruction of the cell and its autolysis, with the latter being accompanied by an inflammation phenomenon. Necrosis occurs in a passive and incidental manner. Tissue necrosis is generally due to the cells being subjected to a physical trauma, or due to a chemical poison, for example.

The other form of cell death is termed apoptosis [Kerr, J. F. R. and Wyllie, A. H., Br. J. Cancer, 265, 239 (1972)]; however, contrary to necrosis, apoptosis does not result in any inflammation phenomenon. Apoptosis has been reported to be able to take place under various physiological conditions. It is a highly selective form of cell suicide which is characterized by readily observable morphological and biochemical phenomena. Thus, condensation of the chromatin, which is or is not associated with an endonuclease activity, formation of apoptotic bodies and fragmentation of the deoxyribonucleic acid (DNA), by activation of endonucleases, into 180–200 base pair DNA fragments (these fragments can be observed by means of agarose gel electrophoresis) are, in particular, observed.

Apoptosis can be regarded as being a programmed cell death which is involved in tissue development, differentiation and renewal. It is also thought that the differentiation, growth and maturation of cells are closely linked to apoptosis and that the substances which are able to play a role in the differentiation, growth and maturation of cells are also linked to the phenomenon of apoptosis.

In the medical field, some pathological situations exhibit a modified, if not deregulated, apoptosis mechanism. Thus, it has been reported that deliberate modulation of apoptosis, by inducing it or suppressing it, can make it possible to treat a large number of diseases, more specifically diseases linked to cell hyperproliferation, as in the case of cancer, autoimmune diseases and allergies, or, on the other hand, diseases which are linked to cell disappearance, as in the case of the human immunodeficiency virus (HIV) immunodeficiency syndrome, neurodegenerative diseases (Alzheimer's disease) or excessive damage which is induced during myocardial infarction.

Specifically, it has been noted in oncology that a large number of antineoplastic drugs, such as dexamethasone, cyclophosphamide and cisplatin, are able to induce apoptosis.

In the cosmetic field, the signs of cutaneous ageing essentially result from dysfunction of the principal biological mechanisms of the skin which, in particular, bring the mechanism of apoptosis into play. It is possible, therefore, to imagine that any product which induces the mechanism of apoptosis is a product which is suitable for preventing and/or combating the appearance of ageing and the existing signs of ageing such as large and small wrinkles.

In the field of retinoids, it is known that all-trans retinoic acid is a powerful modulator (i.e. an inhibitor or, on the other hand, a stimulator, depending on the nature of the cells which are treated) of the differentiation and proliferation of many normal or transformed cell types. For example, it inhibits the differentiation of epithelial cells such as the keratinocytes of the epidermis. It also inhibits the proliferation of many transformed cells such as melanoma cells. These effects on proliferation and differentiation can affect one and the same type of cell simultaneously, as is the case, for example, for HL-60 human promyelocytic cells; thus, it is known that proliferation of these cells is inhibited by all-trans retinoic acid and that, at the same time, their differentiation into granulocytes and their apoptosis are induced.

It is known, in a general manner, that all-trans retinoic acid acts on the differentiation and proliferation of cells by interacting with nucleoreceptors which are termed RARs (retinoic acid receptors) and which are present in the cell nucleus. To date, three subtypes of RAR receptors, termed RAR-α, RAR-β and RAR-γ, respectively, have been identified. After having bound the ligand (i.e. all-trans retinoic acid), these receptors interact with specific response elements (RARE) in the promoter region of genes which are regulated by retinoic acid. In order to bind to the response elements, the RARs heterodimerize with another type of receptor known as RXR receptors. The natural ligand of the RXRs is 9-cis-retinoic acid. The RXRs are regarded as being master regulatory proteins because they interact with other members of the steroid/thyroid receptor superfamily, such as the receptor for vitamin D3 (VDR), the receptor for triiodothyroxine (TR) and the PPARs (peroxisome proliferator activated receptors), to form heterodimers, as they do with the RARS. Furthermore, the RXRs are able to interact with specific response elements (RXRE) in the form of homodimers. These complex interactions, and the existence of numerous RAR and RXR receptors which are expressed differently depending on the tissue and the cell type, explain the pleiotropic effects of retinoids in virtually all cells.

Large numbers of synthetic structural analogues of all-trans retinoic acid or of 9-cis-retinoic acid, commonly termed "retinoids", have so far been described in the literature. Some of these molecules are able to bind to, and specifically activate, the RARs or, on the other hand, the RXRs. Furthermore, some analogues are able to bind to, and activate, a particular subtype (α, β or γ) of RAR receptor. Finally, other analogues do not exhibit any particular selective activity with regard to these different receptors. In this respect, and by way of example, 9-cis-retinoic acid activates both the RARs and the RXRs without any noteworthy selectivity for either of these receptors (nonspecific agonist ligand), whereas all-trans retinoic acid selectively activates the RARs (RAR-specific agonist ligand) without regard to subtype. In a general manner, and qualitatively, a given substance (or ligand) is said to be specific for a given receptor family (or with regard to a particular receptor of this family) when the said substance exhibits an affinity for all the receptors of this family (or, respectively, for the particular receptor of this family) which is stronger than that which it otherwise exhibits for all the receptors of any other family (or, respectively, for all the other receptors, of this same family or not).

It has been reported that 9-cis-retinoic acid and all-trans retinoic acid are modulators of apoptosis (activator or inhibitor of apoptosis depending, in particular, on the cell type) and that 9-cis-retinoic acid is the more active of these two modulators, with it being possible to explain this observation by the fact that 9-cis-retinoic acid activates both the RARs and the RXRS, contrary to all-trans retinoic acid, which only activates the RARS.

In view of that which has been previously stated, it appears to be of interest to find novel modulators of apoptosis.

In this regard, the Applicant has just discovered that agonist ligands which are specific for receptors of the RAR-γ type are excellent inducers of apoptosis in a variety of cell types, more specifically in thymocytes.

Thus, the present invention relates to the use of at least one agonist ligand which is specific for receptors of the RAR-γ type in the preparation of a pharmaceutical composition which is intended to increase the rate of apoptosis in at least one cell population in which apoptosis can be induced by activating receptors of the RAR-γ type.

The invention also relates to the use, in a cosmetic composition, of at least one agonist ligand which is specific for receptors of the RAR-γ type as an inducer of apoptosis in at least one cell population of the skin in which apoptosis can be induced by activating receptors of the RAR-γ type.

Thus, this composition can make it possible to prevent and/or combat photoinduced or chronological ageing of the skin, in particular by eliminating, by means of apoptosis, cells of the skin which exhibit a deficiency in their repair function and which accumulate over time.

The invention therefore relates, finally, to a cosmetic process for preventing and/or combating photoinduced or chronological ageing of the skin, characterized in that an apoptosis-inducing cosmetic composition, such as previously described, is applied to the skin.

The pharmaceutical or cosmetic composition according to the invention comprises a physiologically acceptable medium.

Agonist ligand which is specific for receptors of the RAR-γ type is understood, according to the invention, as meaning any agonist ligand which exhibits a ratio R of the dissociation constant of this ligand for receptors of the RAR-α type over the dissociation constant of this ligand for receptors of the RAR-γ type which is greater than or equal to 10, and which induces differentiation of F9 cells.

Thus, it is known that all-trans retinoic acid and some of its analogues are able to induce the differentiation of mouse embryonic teratocarcinoma cells (F9 cells); they are therefore regarded as being agonists for the RAR receptors. The secretion of the plasminogen activator which accompanies this differentiation is an index of the biological response of the F9 cells to the retinoids (Skin pharmacol. 1990; 3: pp. 256–267).

The dissociation constants are determined by means of tests which are standard for the skilled person. These tests are described, in particular, in the following references: (1) "Selective Synthetic Ligands for Nuclear Retinoic Acid Receptor Subtypes" in RETINOIDS, Progress in Research and Clinical Applications, Chapter 19 (pp 261–267), Marcel Dekker Inc., edited by Maria A. Livrea and Lester Packer; (2) "Synthetic Retinoids: Receptor Selectivity and Biological Activity" in Pharmacol Skin, Basel, Karger, 1993, Volume 5, pp 117–127; (3) "Selective Synthetic Ligands for Human Nuclear Retinoic Acid Receptors" in Skin Pharmacology, 1992, Vol. 5, pp 57–65; (4) "Identification of Synthetic Retinoids with Selectivity for Human Nuclear Retinoic Acid Receptor-γ" in Biochemical and Biophysical Research Communications, Vol. 186, No. 2, July 1992, pp 977–983; (5) "Selective High Affinity RAR-α or RAR-β Retinoic Acid Receptor Ligands" in Mol. Pharmacol., Vol. 40, pp 556–562.

Other characteristics, aspects, aims and advantages of the invention will become even clearer from reading the description which follows as well as the various specific examples, which are intended as an illustration and in no way as being limiting.

Agonist ligands which are specific for receptors of the RAR-γ type, and which may be mentioned, are 6-3-(1-adamantyl)-4-hydroxyphenyl)-2-naphthanoic acid, (E)-4-(1-hydroxy-1-(5,6,7,8-tetra-hydro-5,5,8,8-tetramethyl-2naphthyl)-2-propenyl)benzoic acid, 4-[(E)-2-(3-(1-adamantyl)-4-hydroxyphenyl)-1-propenyl]benzoic acid, 5',5',8',8'-tetramethyl-5',6',7',8'-tetrahydro-[2,2']binaphthalenyl-6-carboxylic acid, 2-(5,5,8,8-tetramethyl-5,6,7,8-tetrahydro-naphthalen-2-yl)-benzo [b]thiophene-6-carboxylic acid, 4-(5,5,8,8-tetramethyl-5,6,7,8-tetrahydro-naphtho[2,3-b]thiophen-2-yl)benzoic acid, 6-(5,5,8,8-tetramethyl-5,6,7,8-tetrahydro-naphthalene-2-carbonyl)naphthalene-2-carboxylic acid, 3,7-dimethyl-7-(1,2,3,4-tetrahydro-1,4a,9b-trimethyl-1,4-methano-dibenzofuran-8-yl)-2,4,6-heptatrienoic acid, 6-(1,2,3,4-tetrahydro-1,4a,9b-trimethyl-1,4-methano-dibenzofuran-8-yl)-naphthalene-2-carboxylic acid, 6-[hydroxyimino-(5,5,8,8-tetramethyl-5,6,7,8-tetra-hydro-naphthalen-2-yl)-methyl]naphthalene-2-carboxylic acid, 4-[(6-hydroxy-7-(1-adamantyl)-2-naphthyl]benzoic acid, 5-(5,5,8,8-tetramethyl-5,6,7,8-tetrahydro-anthracen-2-yl)-thiophene-2-carboxylic acid, (-)-6-[hydroxy-(5,5,8,8-tetramethyl-5,6,7,8-tetrahydro-naphthalen-2-yl)-methyl]-naphthalene-2-carboxylic acid, 6-(3-adamantan-1-yl-4-prop-2-ynyloxy-phenyl)-naphthalene-2-carboxylic acid, 4-[(2-oxo-2-(5,5,8,8-tetramethyl-5,6,7,8-tetrahydro-naphthalen-2-yl)-ethoxy]-benzoic acid, 4-[2-oxo-2-(5,5,8,8-tetramethyl-5,6,7,8-tetrahydro-naphthalen-2-yl)-acetylamino]-benzoic acid, 4-[2-fluoro-2-(5,5,8,8-tetramethyl-5,6,7,8-tetrahydro-naphthalen-2-yl)-acetylamino]-benzoic acid, 6-[3-(1-adamantyl-4-(2-hydroxypropyl)phenyl]-2-naphthoic acid, 5-[3-oxo-3-(5,5,8,8-tetramethyl-5,6,7,8-tetrahydro-naphthalen-2-yl)-propenyl]-thiophene-2-carboxylic acid, 6-[3-(1-adamantyl-4-(2,3-di-hydroxypropyl)phenyl]-2-naphthoic acid, 4-[3-hydroxy-(5,6,7,8-tetrahydro-5,5,8,8-tetramethyl-2-naphthyl)-1-propynyl]-benzoic acid, 4-[3-oxo-3-(5,5,8,8-tetramethyl-5,6,7,8-tetrahydro-naphthalen-2-yl)-prop-1-ynyl]benzoic acid, 4-[(3-(1-methylcyclohexyl)-4-hydroxyphenyl)ethenyl]-benzoic acid, 4 [(E)2-(3-(1-adamantyl)-4-hydroxyphenyl-ethenyl]-benzoic acid, 4-[3-(1-adamantyl)-4-hydroxyphenylethynyl)-benzoic acid, 5-[3-(1-adamantyl)-4-hydroxyphenylethynyl]-2-thiophenecarboxylic acid, 5-[3-(1-adamantyl)-4-methoxyphenylethynyl]-2-thiophene-carboxylic acid, 4-[2-(3-tert-butyl-4-methoxyphenyl)-propenyl]benzoic acid, 4-(2-[4-methoxy-3-(1-methyl-cyclohexyl)phenyl]-propenyl)-benzoic acid, 6-[3-(1-adamantyl)-4-(3-methoxy-2-hydroxypropyl)-phenyl]-2-naphthoic acid, 2-hydroxy-4-[3-hydroxy-3-(5,6,7,8-tetrahydro-5,5,8,8-tetramethyl-2-naphthyl)-1-propynyl]-benzoic acid, 6-(5,5,8,8-tetramethyl-5,6,7,8-tetrahydro-naphthalen-2-yloxy)-naphthalene-2-carboxylic acid, 6-(5,5,8,8-tetramethyl-5,6,7,8-tetrahydro-naphthalen-2-ylsulphanyl)-naphthalene-2-carboxylic acid, 4-[2-propoxyimino-2-(5,5,8,8-tetramethyl-5,6,7,8-tetrahydro-naphthalen-2-yl)-acetylamino]benzoic acid, 6-(5,5,8,8-tetramethyl-5,6,7,8-tetrahydro-naphthalen-2-ylamino)naphthalene--2-carboxylic acid, 1-methyl-4-(5,5,8,8-tetramethyl-5,6,7,8-tetrahydroanthracen-2-yl)-1H-pyrrole-2-carboxylic acid, 2-methoxy-4-(5,5,8,8-tetramethyl-5,6,7,8-tetrahydro-anthracen-2-yl)-benzoic acid, 4-[2-nonyloxyimino-2-(5,5,8,8-tetramethyl-5,6,7,8-tetrahydro-naphthalen-2-yl)-acetylamino]-benzoic acid, (-)-2-hydroxy- 4-[3-hydroxy-3-(5,5,8,8-tetramethyl-5,6,7,8-tetrahydro-naphthalen-2-yl)-prop-1-ynyl]-benzoic acid, (+)-2-hydroxy-4-[3-hydroxy-3-(5,5,8,8-tetramethyl5,6,7,8-tetrahydro-naphthalen-2-yl)-prop-1-ynyl]-benzoic acid, 2-hydroxy-4-[3-hydroxy-3-(5,5,8,8-tetramethyl-5,6,7,8-tetrahydro-naphthalen-2-yl)-but-1-yriyl]-benzoic acid, 6-(3-bromo-5,5,8,8-tetramethyl-5,6,7,8-tetrahydro-naphthalen-2-yloxy)-naphthalene-2-carboxylic acid, 3-[(5,6,7,8-tetrahydro-5,5,8,8-tetramethyl-2-naphthyl)-2H-1-benzopyran]-7-carboxylic acid, 4-[3-(3,5-di-tert-butyl-4-hydroxy-phenyl)-prop-1-ynyl]-benzoic acid, 4-[3-(5,5,8,8-tetra-methyl-5,6,7,8-tetrahydro-naphthalen-2-yl)-prop-1-ynyl]-benzoic acid, 4-[3-(5,6,7,8-tetrahydro-5,5,8,8-tetramethyl-2-naphthyl)-1-propynyl]-salicylic acid, 4-[{3-(1-adamantyl)-4-(2-hydroxyethyl)phenyl}ethynyl]-benzoic acid and 4-[{3-(1-adamantyl)-4-(3-hydroxy-propyl)phenyl}ethynyl]-benzoic acid.

Preference is given, in the present invention, to using agonist ligands which are specific for receptors of the RAR-γ type which exhibit a ratio R which is greater than or equal to 50. As such, preference is given to using 6–3-(1-adamantyl)-4-hydroxyphenyl)-2-naphthanoic acid, 6-(5,5,8,8-tetra-methyl-5,6,7,8-tetrahydro-naphthalene-2-carbonyl)-naphthalene-2-carboxylic acid, 6-(1,2,3,4-tetrahydro-1,4a,9b-trimethyl-1,4-methano-dibenzofuran-8-yl)-naphthalene-2-carboxylic acid, 6-[hydroxyimino-(5,5,8,8-tetramethyl-5,6,7,8-tetrahydro-naphthalen-2-yl)-methyl]-naphthalene-2-carboxylic acid, 5-(5,5,8,8-tetramethyl-5,6,7,8-tetrahydro-anthracen-2-yl)-thiophene-2-carboxylic acid, (-)-6-[hydroxy-(5,5,8,8-tetramethyl-5,6,7,8-tetrahydro-naphthalen-2-yl)-methyl]-naphthalene-2-carboxylic acid, 6-[3-(1-adamantyl-4-(2-hydroxypropyl)phenyl]-2-naphthoic acid, 6-[3-(1-adamantyl-4-(2,3-di-hydroxypropyl)phenyl]-2-naphthoic acid, 4-[3-(1-adamantyl)-4-hydroxyphenylethynyl]-benzoic acid, 5-[3-(1-adamantyl)-4-hydroxyphenylethynyl]-2-thiophenecarboxylic acid, 5-[3-(1-adamantyl)-4-methoxyphenylethynyl]-2-thiophenecarboxylic acid, 6-[3-(1-adamantyl)-4-(3-methoxy-2-hydroxypropyl)-phenyl]-2-naphthoic acid, 1-methyl-4-(5,5,8,8-tetra-methyl-5,6,7,8-tetrahydro-anthracen-2-yl)-1H-pyrrole-2-carboxylic acid, (−)-2-hydroxy-4-[3-hydroxy-3-(5,5,8,8-tetramethyl-5,6,7,8-tetrahydro-naphthalen-2-yl)-prop-1-ynyl]-benzoic acid and 2-hydroxy-4-[3-hydroxy-3-(5,5,8,8-tetramethyl-5,6,7,8-tetrahydro-naphthalen-2-yl)-but-1-ynyl)-benzoic acid.

6–3-(1-Adamantyl)-4-hydroxyphenyl)-2-naphthanoic acid is particularly preferred.

Thus, it will be possible to use the pharmaceutical composition comprising the agonist ligand which is specific for receptors of the RAR-γ type when it is necessary to increase the rate of apoptosis. Naturally, this effect will only be achieved in cell populations in which apoptosis can be induced by activating receptors of the RAR-γ type and therefore, in particular, in which receptors of the RAR-γ type are present, as is the case, more specifically, in cells derived from the thymus.

It may prove to be necessary to increase the rate of apoptosis in two cases in the main. The first case relates to diseases or disorders which are linked to an inadequate rate of apoptosis. The second case relates to treatments which are required during a transplantation in order to decrease the effects tending to reject the transplanted organ. Thus, it is possible to consider increasing immunotolerance to the transplanted organ by decreasing the immune response of the T cells by means of inducing their rate of apoptosis.

Diseases or disorders which are linked to an inadequate rate of apoptosis, and which may more specifically be mentioned, are disorders which are due to precancerous conditions or cancers which can be the consequence of a proliferation of certain cell populations, autoimmune diseases, allergies or inflammatory reactions in which the number of cells causing damage is observed to be too high, or else in certain viral infections in which proteins of the virus have an antiapoptotic effect. Thus, in the case of autoimmune diseases, more specific mention may be made of insulin-dependent diabetes, active chronic hepatitis, rheumatoid arthritis, pemphigus, multiple sclerosis, myasthenia, systemic lupus erythematosus, Crohn's disease and psoriasis. Actinic keratosis may be mentioned with regard to precancerous conditions. In the case of cancer, more specific mention may be made of lymphomas, carcinomas, such as cancer in the ENT sphere, and hormone-dependent tumours, such as ovarian cancers. Of the abovementioned viral infections, those which may in particular be cited are herpesviruses, adenoviruses and variola viruses (poxviruses). Allergies or inflammatory reactions which may be mentioned are contact eczema, atopic eczema, asthma and urticarias.

The composition according to the invention can be administered by the enteral, parenteral, topical or ocular route. Preference is given to packaging the pharmaceutical composition in a form which is suitable for administration by the systemic route (for injection or perfusion).

When administered by the enteral route, the composition, more specifically the pharmaceutical composition, can be in the form of tablets, hard gelatin capsules, coated tablets, syrups, suspensions, solutions, powders, granules, emulsions, microspheres or nanospheres, or lipid or polymeric vesicles which permit a controlled release. When administered by the parenteral route, the composition may be in the form of solutions or suspensions for perfusion or injection.

The agonist ligands which are specific for receptors of the RAR-γ type and which are used in accordance with the invention are generally administered in a daily dose of from 0.01 mg/kg to 100 mg/kg of bodyweight, with the dose being given in from 1 to 3 administrations.

When administered by the topical route, the pharmaceutical or cosmetic composition according to the invention is more specifically intended for treating the skin and the mucous membranes and can be in the form of ointments, creams, milks, pomades, powders, imbibed buffers, solutions, gels, sprays, lotions or suspensions. It may also be in the form of microspheres or nanospheres, or lipid or polymeric vesicles, or of polymeric patches and hydrogels, which permit a controlled release. This composition, which is administered by the topical route, can be present either in anhydrous form or in aqueous form.

When administered by the ocular route, the composition is chiefly in the form of eye drops.

The agonist ligands which are specific for receptors of the RAR-γ type are used by the topical or ocular route at a concentration which is generally between 0.001% and 10% by weight, preferably between 0.1 and 1% by weight, based on the total weight of the composition.

The present invention finally relates to a process for preventing and/or combating photoinduced or chronological ageing of the skin, characterized in that a cosmetic composition which induces apoptosis such as previously described, that is to say which comprises at least one agonist ligand which is specific for receptors of the RAR-γ type in a cosmetically acceptable medium, is applied to the skin.

Naturally, the compositions as previously described may additionally comprise inert or even pharmacodynamically active additives or combinations of these additives, in particular: wetting agents; depigmenting agents such as hydroquinone, azelaic acid, caffeic acid or kojic acid; emollients; moisturizing agents such as glycerol, PEG 400, thiamorpholinone and its derivatives, or urea; antiseborrhoeic agents or anti-acne agents, such as S-carboxymethylcysteine, S-benzyl-cysteamine, and their salts or derivatives, or benzoyl peroxide; antifungal agents such as ketoconazole or the polymethylene-4,5-isothioazolidonin-3-ones; antibacterial agents, carotenoids and, in particular, β-carotene; antpsoriatic agents such as anthralin and its derivatives; and, finally, eicosa-5,8,11,14-tetraynoic and eicosa-5,8,11-trynoic acids, and their esters and amides.

These compositions may also comprise taste-improving agents, preservatives such as esters of parahydroxybenzoic acid, stabilizers, moisture-regulating agents, pH-regulating agents, agents for modifying the osmotic pressure, emulsifying agents, UV-A and UV-B filters, antioxidants, such as α-tocopherol, butylhydroxyanisole or butylhydroxytoluene.

Naturally, the skilled person will ensure that the possible compound(s) to be added to these compositions is/are selected such that the advantageous properties which are intrinsically attached to the present invention are not altered, or are not substantially altered, by the addition which is envisaged.

Several examples which are intended to illustrate the present invention, but which are in no way limiting, will now be given.

EXAMPLE 1

This experiment demonstrates the in-vivo efficacy of an agonist ligand which is specific for RAR-γ as an inducer of apoptosis. 4-week-old male NMRI mice (sold by LATI, Gödöllo, Hungary) were used. In order to induce apoptosis in the thymus, these male mice were treated by a single injection with either 0.5 mg of dexamethasone, or 0.5 mg of 6-3-(1-adamantyl)-4-hydroxyphenyl)-2-naphthanoic acid, dissolved in a mixture of 0.8 ml of physiological saline and 0.2 ml of ethanol.

Dexamethasone is a well-known inducer of apoptosis. Thus, involution of the thymus is observed: i.e. a decrease of approximately 75% in the weight of the thymus at 48 hours after the abovementioned treatment. A similar effect is observed with 6-3-(1-adamantyl)-4-hydroxyphenyl)-2-naphthanoic acid, with in this case a decrease of approximately 60% in the weight of the thymus being observed at 48 hours after treatment.

In addition, in a similar manner to this test, thymus samples were removed from untreated or treated animals at different times after the treatment. After washing and homogenization, their transglutaminase activity was determined by detecting the incorporation of [$^3$H]putrescine into N,N'-dimethylcasein. The activity of the transglutaminase is calculated in nmoles of [$^3$H]putrescine incorporated into the protein per hour. Tissue transglutaminase has been reported to be one of the elements involved in bringing about apoptosis [Piacentini, M. et al. (1994) Apoptosis: The Molecular Basis of Apoptosis in Disease. Curr. Comm. in Cell & Mol. §Biol. 8 (Tomei L.D. and Cope, F.O. ed) pp. 143–1651]. Thus, it is observed that the above-described involution of the thymus results from treating the mouse with a RAR-γ-specific agonist ligand and is an event which is concomitant with, and proportional to, the activity of the tissue transglutaminase.

Furthermore, this involution of the thymus is correlated with the appearance of DNA fragments following the analysis, by agarose gel electrophoresis, of the DNA which is recovered from this treated thymus (details of the procedure are given in Example 2).

EXAMPLE 2

This example demonstrates the in-vitro efficacy of a RAR-γ-specific agonist ligand as an inducer of apoptosis as compared with other types of retinoid.

Culture and Preparation of the Cells

Thymocyte suspensions are prepared from the thymus glands of untreated four-week-old male NMRI mice (sold by LATI, Gödöllo, Hungary). The medium employed is Sigma RPMI 1640 medium which is supplemented with Gibco foetal calf serum, 2 mM glutamine and 100 IU of penicillin and 100 μg of streptomycin/ml. The thymocytes are then washed, and diluted in order to obtain a final concentration of $10^7$ cells/ml, before being incubated at 37° C. in a humidified incubator under an atmosphere of 5% $CO_2$ and 95% air. Death of the cells is measured by the uptake of trypan blue.

Qualitative and Quantitative Analysis of the DNA

The thymocytes are incubated in 24 wells with various compounds to be tested at different concentrations. After 6 hours of incubation, 0.8 ml of the cell suspensions was lysed by adding 0.7 ml of lysis buffer containing 0.5% (v/v) Triton X-100, 10 mM Tris, 20 mM EDTA, pH 8.0, before being centrifuged at 13,000 g for 15 minutes.

Quantitative analysis of the DNA: the DNA contained in the supernatant (the fragments) and the pellet (intact chromatin) was precipitated with an equivalent quantity of 10% trichloroacetic acid, resuspended in 5% trichloroacetic acid and then quantified using the diphenylamine reagent (Burton, K. (1956) Biochem. J., 62, 315–322).

Qualitative analysis of the DNA: in parallel, the supernatant was precipitated overnight in ethanol containing 0.15 mM NaCl. The pellets are redissolved in a buffer containing 10 mM Tris, 1 mM EDTA, pH 8.0, and these solutions are then treated with RNase; they are then sequentially extracted with an equal volume of phenol and chloroform/isoamyl alcohol (24/1), after which the DNA is precipitated in ethanol before being electrophoresed for 3 hours at 60 V in a 1.8% agarose gel. The DNA fragments were then visualized with UV light after the gel had been stained with ethidium bromide. The gels which are obtained present the picture of a ladder of DNA fragments which are multiples of from 180 to 200 base pairs and which are typical of an apoptosis induction. Throughout the experiments, the degree of fragmentation correlates with the number of cells which are dead and positive to the trypan blue test.

The results of the quantitative analysis are assembled in Table 1 below.

TABLE 1

| Compounds | RAR-α Kd | RAR-γ Kd | R | Quantities of compounds (nM) | % of DNA fragments |
|---|---|---|---|---|---|
| ATRA | 15.5 | 3 | 5.16 | $10^{-8}$ | 2 |
|  |  |  |  | $10^{-6}$ | 4 |
| 9-cisRA | 7 | 17 | 0.41 | $10^{-8}$ | 4 |
|  |  |  |  | $10^{-6}$ | 15 |
| CD437 | 6500 | 77 | 84.42 | $10^{-8}$ | 12 |
|  |  |  |  | $10^{-6}$ | 22 |
| CD666 | 2240 | 68 | 32.94 | $10^{-8}$ | 10 |
|  |  |  |  | $10^{-6}$ | 20 |
| CD2325 | 1144 | 53 | 21.58 | $10^{-8}$ | 5 |
|  |  |  |  | $10^{-6}$ | 20 |

TABLE 1-continued

| Compounds | RAR-α Kd | RAR-γ Kd | R | Quantities of compounds (nM) | % of DNA fragments |
|---|---|---|---|---|---|
| CD2019 | 1100 | 160 | 6.87 | $10^{-8}$ | 0 |
|  |  |  |  | $10^{-6}$ | 15 |

ATRA is all-trans retinoic acid
9-cisRA is 9-cis-retinoic acid
CD437 is 6-3-(1-adamantyl)-4-hydroxyphenyl)-2-naphthanoic acid,
CD666 is (E)-4-(1-hydroxy-1-(5,6,7,8-tetrahydro-5,5,8,8-tetramethyl-2-naphthyl)-2-propenyl)benzoic acid,
CD2325 is 4-[(E)-2-(3-(1-adamantyl)-4-hydroxyphenyl)-1-propenyl] benzoic acid,
CD2019 is 6-(3-(1-methylcyclohexyl)-4-methoxyphenyl)-2-naphthanoic acid The percentage of DNA fragments in this table corresponds to the difference between the percentage of DNA fragments obtained in treated thymocytes and the percentage of DNA fragments obtained in nontreated thymocytes (basal rate of apoptosis for these thymocytes).

These results demonstrate that the percentage appearance of DNA fragments increases as R increases. Thus, the apoptosis-inducing effect increases as the specificity of the ligand for RaR-γ increases.

What is claimed is:

1. A method of cosmetically or therapeutically treating a disease or disorder in at least one cell population wherein the disease pathology is linked to an inadequate rate of apoptosis, with the proviso that said disease is not a cancer or precancer, comprising administering to said cell population a therapeutically effective amount of 6-3-(1-adamantyl)-4-hydroxyphenyl)-2-naphthanoic acid.

2. The method of claim 1, wherein the disease or condition is selected from the group consisting of autoimmune diseases, allergies, inflammatory reactions, and viral infections.

3. The method of claim 1, wherein the disease or condition is an autoimmune disease selected from the group consisting of insulin-dependent diabetes, rheumatoid arthritis, active chronic hepatitis, pemphigus, multiple sclerosis, myasthenia, systemic lupus erythematosus, Chron's disease and psoriasis.

4. The method of claim 1, where the disease is a viral infection selected from the group consisting of herpes virus infection, adenoviral infection, and variola (poxvirus) infection.

5. The method of claim 1, wherein the disease or condition is an allergy or inflammatory disease or condition selected from the group consisting of contact eczema, atopic eczema, asthma, and urticaria.

6. The method of claim 5, wherein topical administration is effected using a dosage form selected from the group consisting of ointments, creams, milks, pomades, powder, imbibed buffers, solutions, gels, sprays, lotions, suspensions, microspheres or nanospheres, lipid or polymeric vesicles, and polymeric patches, or hydrogels.

7. The method of claim 6, wherein said dosage form is an anhydrous or aqueous form.

8. The method of claim 1, wherein said 6-3-(1-adamantyl)-4-hydroxyphenyl)-2-naphthanoic acid is administered by a route selected from the group consisting of enteral, parenteral, topical, ocular, and systemic.

9. The method of claim 8, wherein said systemic route is by injection or perfusion.

10. The method of claim 8, wherein ocular administration is effected using eye drops.

11. The method of claim 1, wherein said 6-3-(1-adamantyl)-4-hydroxyphenyl)-2-naphthanoic acid is administered in a form selected form the group consisting of coated or uncoated tablets, gelatin capsules, syrups, suspensions, solutions, powders, granules, emulsions, microspheres or nanospheres, lipid or polymeric vesicles, solutions, and suspensions.

12. The method of claim 1, wherein the dosage of said 6-3-(1l-adamantyl)-4-hydroxyphenyl)-2-naphthanoic acid is a daily dosage ranging from 0.01 mg/kg to 100 mg/kg of by weight.

13. The method of claim 12, wherein said daily dosage is given in one to three administrations.

14. The method of claim 1, wherein said 6-3-(1-adamantyl)-4-hydroxyphenyl)-2-naphthanoic acid compound is administered topically or ocularly by administration of a composition comprising 0.001% to 10% by weight of said compound.

15. The method of claim 1, which is used to treat or prevent rejection of an organ transplant.

16. The cosmetic method of claim 1, which is used to treat and/or prevent photoinduced or chronologic aging of the skin by topical administration of a cosmetic composition containing an effective amount of 6-3-(1-adamantyl)-4-hydroxyphenyl)-2-naphthanoic acid and a cosmetically acceptable medium.

17. The method of claim 1, wherein said 6-3-(1-adamantyl)-4-hydroxyphenyl)-2-naphthanoic acid compound induces apoptosis by activating receptors of the RAR-γ type.

18. The method of claim 17, wherein said compound which activates receptors of the RAR-γ type possesses a dissociation constant R which is greater than or equal to 50, which is the ratio of binding of the compound to receptors of the RAR-α type relative to receptors of the RAR-γ type.

* * * * *